United States Patent
Hansen et al.

(10) Patent No.: US 10,278,857 B2
(45) Date of Patent: May 7, 2019

(54) OSTOMY APPLIANCE

(71) Applicant: Coloplast A/S, Humlebaek (DK)

(72) Inventors: Michael Hansen, Gilleleje (DK);
Esben Stroebech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 660 days.

(21) Appl. No.: 14/764,033

(22) PCT Filed: Jan. 28, 2014

(86) PCT No.: PCT/DK2014/050017
§ 371 (c)(1),
(2) Date: Jul. 28, 2015

(87) PCT Pub. No.: WO2014/117778
PCT Pub. Date: Aug. 7, 2014

(65) Prior Publication Data
US 2015/0359656 A1 Dec. 17, 2015

(30) Foreign Application Priority Data

Jan. 29, 2013 (DK) .................................. 2013 70049

(51) Int. Cl.
*A61F 5/44* (2006.01)
*A61F 5/443* (2006.01)
*A61F 5/445* (2006.01)
*A61F 5/448* (2006.01)

(52) U.S. Cl.
CPC ............ *A61F 5/4404* (2013.01); *A61F 5/443* (2013.01); *A61F 5/445* (2013.01); *A61F 2005/4483* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,074,404 A | * | 1/1963 | Robinson | A61F 5/448 604/338 |
| 4,109,657 A | * | 8/1978 | Carrington | A61F 5/448 604/338 |
| 4,834,731 A | * | 5/1989 | Nowak | A61F 5/448 604/339 |

(Continued)

FOREIGN PATENT DOCUMENTS

| | | |
|---|---|---|
| CN | 201005837 Y | 1/2008 |
| EP | 0812583 A1 | 12/1997 |

(Continued)

*Primary Examiner* — Tatyana Zalukaeva
*Assistant Examiner* — Guy K Townsend
(74) *Attorney, Agent, or Firm* — Coloplast Corp., Coloplast A/S; Nick Baumann

(57) ABSTRACT

A one-piece or two-piece ostomy appliance comprising a base plate (1), the base plate comprising an adhesive wafer (11) that comprises a top film (8) and at least one skin-friendly adhesive (9) on a proximal surface thereof, for attaching the base plate to the skin of a user, and a first through-going-hole (5). Further, a convex element (10) is arranged distal to a user-interface of the adhesive wafer and has a second through-going hole (15) of the same diameter as the first through-going hole and being co-axially arranged therewith. The convex element comprises a material which reacts to moisture.

20 Claims, 4 Drawing Sheets

(56) References Cited

U.S. PATENT DOCUMENTS

| | | | |
|---|---|---|---|
| 5,000,748 A * | 3/1991 | Fenton | A61F 5/443 604/340 |
| 5,316,607 A * | 5/1994 | Johnsen | A61F 5/443 156/212 |
| 5,429,625 A * | 7/1995 | Holmberg | A61F 5/448 604/338 |
| 5,607,413 A * | 3/1997 | Holmberg | A61F 5/448 604/332 |
| 6,569,134 B1 * | 5/2003 | Leise, Jr. | A61F 5/448 604/332 |
| 6,673,056 B2 * | 1/2004 | Metz | A61F 5/448 604/332 |
| 6,790,200 B2 * | 9/2004 | Fenton | A61F 5/445 604/332 |
| 6,863,663 B1 * | 3/2005 | Mills | A61F 5/443 604/337 |
| 7,214,217 B2 * | 5/2007 | Pedersen | A61F 5/441 604/332 |
| 2008/0300556 A1 * | 12/2008 | Fenton | A61F 5/4404 604/339 |
| 2010/0174253 A1 * | 7/2010 | Cline | A61F 5/445 604/328 |
| 2011/0015475 A1 * | 1/2011 | Hanuka | A61F 2/04 600/32 |
| 2012/0143155 A1 * | 6/2012 | Edvardsen | A61F 5/4404 604/318 |
| 2014/0316360 A1 * | 10/2014 | Ekfeldt | A61F 5/445 604/344 |
| 2015/0359656 A1 * | 12/2015 | Hansen | A61F 5/443 604/344 |
| 2016/0256665 A1 * | 9/2016 | Doshi | F16M 13/022 |
| 2017/0020712 A1 * | 1/2017 | Becker | A61F 5/443 |

FOREIGN PATENT DOCUMENTS

| | | |
|---|---|---|
| EP | 1163892 A2 | 12/2001 |
| GB | 249897 A | 4/1926 |
| JP | 2003126133 A2 | 5/2003 |
| RU | 2220685 C1 | 1/2004 |
| WO | 9318725 A1 | 9/1993 |
| WO | 0047143 A1 | 8/2000 |
| WO | 0135875 A2 | 5/2001 |
| WO | 03075808 A1 | 9/2003 |
| WO | 06038025 A1 | 4/2006 |
| WO | 10054662 A2 | 5/2010 |
| WO | 2011003420 A1 | 1/2011 |
| WO | 2012079592 A1 | 6/2012 |

* cited by examiner

OSTOMY APPLIANCE

The present invention relates to ostomy appliances. In particular, the invention relates to a base plate of an ostomy appliance comprising a convex element and the use thereof. More particularly, the invention relates to a material of a convex element that changes characteristics when exposed to moisture.

BACKGROUND

Base plates are used in ostomy appliances to attach ostomy bags to the skin of a user having a stoma, the user also being referred to as an ostomist.

A base plate is typically formed by a backing layer or top film on which a skin friendly adhesive is disposed. A through-going hole is arranged in the base plate to receive a stoma so that the base plate may be adhered to the skin surrounding the stoma.

In order to collect output from the stoma, the opening of an ostomy bag is arranged around the through-going hole. The ostomy bag may, for example, be arranged by welding the bag to the backing layer of the base plate. In the art, this is referred to as a one-piece ostomy appliance. Alternatively, a coupling arrangement, typically either adhesive or mechanical, may be arranged so that ostomy bags can be detachably mounted on the base plate. This allows the bag to be changed when full without detaching the base plate from the skin. In the art, this is referred to as a two-piece ostomy appliance.

A number of ostomists develop so-called sunken/retracted stomas. Due to inevitable post-surgical and ongoing physiological changes of the ostomist's body, the stoma may from the outset or over time sink or retract into the abdomen creating a recess in the body surface where the stoma is placed. Applying a standard planar base plate around a retracted stoma would, for one thing, leave the area around the stoma uncovered (gap between the peristomal skin surface and adhesive surface of base plate) and thereby exposed to the output from the stoma. Moreover, in some cases the stoma may be retracted to such a degree that it cannot extend through the through-going hole in the base plate thus resulting in frequent leakage problems. In order to address the issue of retracted stomas, and the encountered frequent leakages, convex base plates have been developed.

Traditionally, such convex base plates are made by providing a relatively stiff pre-cast or moulded unit of convex shape and attaching it to one side of an adhesive wafer whereby the base plate obtains its convexity. Such products have been available on the markets for many years.

The primary purposes and effects of these convex base plates are that they are able to withhold the peristomal skin of the ostomist's body from collapsing (e.g. due to excess skin folds) and to increase the ability of the stoma to protrude adequately past the interface between the base plate and the body surface due to the reactive force provided by them and thus deposit the stomal output directly into a collecting bag for human body wastes. Thereby the risk of leakages is reduced since stomal output is less prone to end up underneath the adhesive surface of the base plate where it may attack and eventually disintegrate the adhesive seal.

Generally, however, since these products are relatively stiff and inflexible, they will not follow the movements of the user's body caused by physical activity very well. More severely, experience has shown that the use of these products may in some cases result in peristomal skin damage such as pressure wound ulceration, bruises and/or general skin irritation.

Moreover, the pre-cast or moulded unit of these convex base plates cannot be fitted to abutment with the stoma or even provided close to the stoma. Instead, they require some radial clearance between the innermost edge of the convex pre-cast or moulded unit and the stoma's surface.

This is due to a number of reasons: first of all, experience has shown that if a stiff unit is in direct contact with the mucus membrane of a stoma's surface, it tends to cut and irritate it, which may eventually cause the stoma to bleed and incur serious complications. Also, the pre-cast or moulded unit may prevent the stoma from expanding freely, the expansion(s) caused by the peristaltic movements of the intestine.

In addition thereto, the presence of such a radial clearance between the innermost edge of the pre-cast or moulded unit and the stoma-receiving through-going hole means that there will be a lack of adequate constant pressure against the skin surface, particularly in the immediate peristomal skin area. This lack of adequate pressure often means that the immediate peristomal skin of the user, between the innermost edge of the convex unit and the stoma's surface, is distanced axially in relation to the skin otherwise forced in position by the convex unit. This phenomenon increases the risk of leakages.

Moreover, almost all users need to perform some sort of customizing action to make a fresh appliance fit as precisely as possible to the shape of their stoma's surface (contour(s)) to provide the best possible security against leakages. To that end, almost every ostomy appliance, including those having a pre-cast or moulded convex unit, has a possibility to cut (e.g. with scissors) in the surface of the base plate to make it fit as good as possible. This is often facilitated by means of a small hole, referred to as a pre-cut hole, starter-hole or simply "pre-cut" provided in the center of the base plate by the manufacturer.

With regard to the traditional convex base plates, the presence of the pre-cast or moulded stiff convex unit sets a limit to the level of customization possible, in terms of the hole size and shape in such products, as it is not possible to cut the pre-cast convex unit.

One example of such a traditional and relatively stiff convex base plate is disclosed in EP748195.

In more recent years an increased variety of convex base plate products have been made available to ostomists. As every user has individual needs due to his or her unique body and stoma shape, experience has shown that the known stiff convex products fail to overcome each and every kind of those needs.

Particularly, if the recess in the body is relatively shallow, i.e. when the stoma is only retracted to a relatively small degree, a less bulky and stiff convex base plate may be appropriate. Furthermore, there has been a desire to alleviate at least some of the user-experienced discomfort caused by the stiffness and inflexibility of the known stiff convex base plates.

To overcome these and other needs, what is commonly accepted as "soft convex" base plates, have been developed. These have a much higher degree of flexibility than the stiff convex base plates and thus improve user comfort.

An example of a construction of such a soft convex base plate product available today comprises at least a layered structure where one layer is a skin friendly adhesive for attachment to an user's body, the adhesive layer being backed by a thermoplastic backing material that is provided at least partly with a convex shape by thermoforming the backing material either before or after application of the adhesive layer. Thus, the product's convexity in this case is achieved by thermoforming the backing into the desired convex shape.

Such soft convex products only provide low pressure to the peristomal skin as their convexity may be considered "reinforced" only by the thermoforming of the backing material. Therefore, they typically cannot increase the ability of the stoma to protrude adequately past the interface between the base plate and the body surface due to the lack of reactive force provided by them.

These soft convex products typically do not have any radial clearance between an innermost part of the thermoformed backing and the through-going hole, as the backing supports the adhesive over the whole surface thereof (in other words, the backing is the convexity providing element). Having to cut directly in the convex thermoformed backing material for customization to the stoma's surface, increases the risk of the resulting (cut) edge of the backing material harming and/or irritating the stoma's surface.

An example of a type of soft convex base plate is disclosed in EP1178766.

In view of the above described available solutions of today, there is a clear need to improve these so as to provide an ostomy appliance that can maintain a relatively constant pressure against the peristomal skin all the way to abutment with the stoma or in very close vicinity thereof while simultaneously provide the user with the possibility of customizing such a product to a very close fit with the shape of the stoma with a minimal risk of cutting and/or irritating the stoma. Particularly, in the case of convex products, the solution according to the present invention provides these advantages while also providing at least some of the flexibility known from soft convex base plates.

SUMMARY OF THE INVENTION

To overcome the drawbacks of the presently available solutions introduced above, the following disclosure presents an inventive base plate comprising a convex element that maintains a significantly higher degree of its initial convexity after being submitted to load than known solutions, while still being customizable to closely fit to the stoma's surface at very little or no risk of the innermost edge of the convex element cutting or otherwise harming the stoma. It is further introduced that a base plate comprising a convex element according to the invention is able to incur a higher reactive force to the peristomal skin of a user than the known solutions. Thereby, the ability to keep the stoma adequately protruding above the surrounding skin level is increased and the risk of stomal output ending up underneath the adhesive in the immediate peristomal area is therefore significantly reduced or eliminated by the invention, which in turn significantly reduces the number of encountered leakage problems for the user.

DETAILED DESCRIPTION OF THE INVENTION

Figure 1:
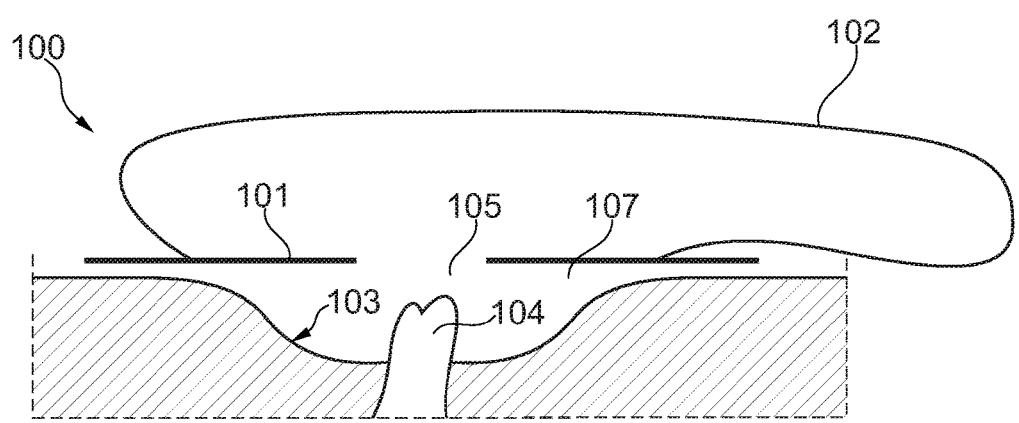
FIG. 1 is a schematic cross-sectional view of an ostomy appliance with a standard type base plate and is intended to at least partly illustrate the limitations of such a product type in regard to a stoma situated in a recess (or concavity) of a skin surface.

For interpretations in the context of the present application, some definitions regarding the subject matter of the attached claims are presented below.

When referring to the proximal side of a device or part of a device, the referral is to the skin-facing side, when the ostomy appliance is worn by a user. Likewise whenever referring to the distal side of a device or part of a device, the referral is to the side facing away from the skin, when the ostomy appliance is worn by a user. In other words, the proximal side is the side closest to the user, when the appliance is fitted on the user and the distal side is the opposite side—the side furthest away from the user in use.

The axial direction, or axially, is defined as the direction of the stoma when the appliance is worn by a user. Thus the axial direction is substantially perpendicular to the abdominal surface of the user.

The radial direction, or radially, is defined as transverse to the axial direction that is transversely to the direction of the stoma.

"Convex" is intended to define that an element or its corresponding surface has a shape or form that provides an overall convexity. In other words, while a smaller section or zone making up part of the overall element or its corresponding surface may have e.g. a linear shape or form, the element or surface as a whole has a convex shape. It is of course to be understood that if for a sheet- or plate-like element one major surface has a convex shape, the opposite major surface may be seen as having a corresponding concave shape.

"User-interface of the adhesive wafer' is intended to define the adhesive surface of the adhesive wafer that engages with the user's skin.

"Release liner" is intended to define a liner covering the proximal side of the adhesive wafer ensuring at least that the properties of the adhesive are preserved and that the adhesive surface is not laid open until just before the use.

In a first aspect, the invention relates to a one-piece or two-piece ostomy appliance comprising a base plate, the base plate comprising an adhesive wafer comprising a top film and at least one skin-friendly adhesive on a proximal surface thereof for attaching the base plate to the skin of a user and having a first through-going hole, and a convex element being arranged distal to the user-interface of the adhesive wafer and having a second through-going hole of the same diameter as the first through-going hole and being co-axially arranged therewith, wherein the convex element comprises a material which reacts to moisture.

According to the invention, an ostomy appliance comprising a base plate with a convex element is effectively achieved that will maintain an adequate and constant pressure in the immediate peristomal skin area, where it is mostly needed, while simultaneously allowing customization of the stoma-receiving through-going hole of the base plate in order to fit an individual stoma shape and in addition being flexible to follow the body movements of a user. Both individually and in combination these effects result in an ostomy appliance having improved security against leakages.

As the convex element of the base plate comprises a material which reacts to moisture, it is ascertained that the edge in the convex element, even when customized by e.g. a user's cutting action to fit with an individual stoma surface, will be smooth and tender and not cut or scratch the stoma surface due to the reaction to moisture. In particular, the material softens, wholly or partly. In other words, the physical characteristics of the material and/or convex element change, see elaboration further below. When the base plate with the convex element is placed close to, or even in abutment with the stoma, and thus contacts the wet mucus membrane of the stoma (and/or moist stomal output), the contacting surface of the (cut) edge of the convex element softens and friction between the convex element and the stoma's surface is significantly reduced. Thus, also the risk of damaging the stoma is greatly reduced or even eliminated with the ostomy appliance according to the invention.

The adhesive wafer comprised in the base plate comprises a top film (or backing layer) carrying or having disposed at least one skin-friendly adhesive on a proximal surface of the top film.

The top film is relatively flexible and may be a thermoplastic blown film primarily based on one or more Ethylene Vinyl Acetate (EVA) materials, one or more thermoplastic polyurethane elastomer (TPU) based materials and/or one or more polyethylene (PE) materials.

The overall thickness of the top film may be in a range of 20-100μ, such as 30-60μ, such as approximately 40μ. In embodiments the film may be a laminate of two or more layers wherein each individual layer may have a thickness of at least 10μ.

One example of at least one skin-friendly adhesive material that may be used for the adhesive wafer according to the invention is a pressure sensitive adhesive composition suitable for medical purposes comprising a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. For further information on such adhesive compositions reference is made to applicant's granted European patent EP1541180B1.

Another example of at least one skin-friendly adhesive material that may be used for the adhesive wafer according to the invention is a second adhesive material comprising a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

Polymers that may be used for the second skin-friendly adhesive will generally be copolymers of ethylene and a polar monomer. The copolymers typically comprise less than about 70% ethylene, have water vapour transmission of more than 50 g/m$^2$/day and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1N), and a water vapour transmission of more than 50 g/m$^2$/day for a 150 μm sheet when measured according to MVTR Test Method (inverted cup method).

Polar oils, which may be used in the invention, will generally be those that have good solubility in the polar domains of the polymer, i.e. provide softness without sacrificing too much tensile strength of the polymer. Oils that can support good water vapour permeability are preferred. Examples of such oils are vegetable and animal oils and derivatives thereof. Preferred polar oils are esters, ethers and glycols and particularly preferred is Poly Propylene Oxide, e.g. alpha-butoxy-polyoxypropylene.

Further information on the types of adhesives suitable for the second skin-friendly adhesive is available in applicant's published application WO 2009/006901A1. More than the two skin-friendly adhesives presented by way of example herein, may be used.

Regardless of the number of skin-friendly adhesives used, an overall average thickness of the skin-friendly adhesive disposed on the top film may be in a range of approximately 0.3-1.5 mm, corresponding to 300μ-1500μ, such as 400μ-1200μ, such as 450μ-800μ, such as 500μ.

The different skin-friendly adhesives may be provided so as to give the adhesive (proximal) surface of the adhesive wafer different characteristics and/or effects. As an example, the different skin-friendly adhesives may comprise smaller or larger amounts of a moisture absorbing component such as hydrocolloids and/or be more or less flexible in relation to each other. The different skin-friendly adhesives may be provided in multiple zones or areas. The zones or areas may have particular suitable shapes or forms depending on the function or effect of the different skin-friendly adhesives.

The convex element of the base plate according to the invention may be made from a material composition blend including one, or some, or all, of the following materials: one or more polyethylene based polymers, one or more ethylene vinyl acetate-based polymers, one or more thermoplastic hydrocolloids, one or more hydrocolloid powders, one or more hydrophilic polyurethane-based polymers, one or more filler materials and/or one or more water swellable/soluble polymers like polyvinylalcohols (PVOH) and copolymers thereof and/or polylactic acids (PLA).

According to the invention, the convex element is arranged distal to the user-interface of the adhesive wafer. This position of the convex element on the adhesive wafer of the base plate may be obtained in different ways.

In a first example thereof, a mixture of materials selected from the above identified list of materials for the convex element is mixed and subsequently the mixture is heat pressed to a desired thickness. An element blank of appropriate size is cut from the pressed material and then attached (e.g. by gluing or welding) to the distal surface of a top film carrying a skin-friendly adhesive on the proximal surface (building the user-interface of the adhesive wafer) and optionally a release liner on the skin-friendly adhesive. This blank is then put in a convex shaped tool in a heat/vacuum moulding machine and submitted to shaping, whereby a base plate with the convex element being arranged distal to the user-interface of the adhesive wafer is generally obtained. A stoma-receiving through-going hole may be punched before or after the described steps. In this way, the convex element is arranged distal to the user-interface of the adhesive wafer. Therefore, in embodiments, the convex element is attached to the top film.

In a second example thereof, again a mixture of materials selected from the above identified list of materials for the convex element is mixed and subsequently the mixture is heat pressed to a desired thickness. As in the first example, an element blank of appropriate size is cut from the pressed material. Then, in contrast to the first example, a distal surface of the cut element blank is attached to the proximal (adhesive) surface of a skin-friendly adhesive on a top film and subsequently a second (which may be the same as the first) skin-friendly adhesive is provided on the proximal surface of at least the cut element blank, thereby effectively positioning the cut element blank between two layers of skin-friendly adhesive(s), but still arranged distal to the user-interface of the adhesive wafer. A release liner may optionally be placed on the proximal surface (building the user-interface of the adhesive wafer). Similarly to the first example, this blank is then put in a convex shaped tool in a heat/vacuum moulding machine and submitted to shaping, whereby a base plate with the convex element being arranged distal to the user-interface of the adhesive wafer (but positioned or embedded between two adhesives) is generally obtained. A stoma-receiving through-going hole may be punched before or after the described steps. Thus, in embodiments, the convex element is embedded between at least two skin-friendly adhesives.

The overall thickness and/or softness of the material of the convex element may at least to some degree be controlled or regulated particularly by the amount and type(s) of filler material(s) used in the element. Filler materials may include clay, aluminiumhydroxide, lime, chalk or other, such as non- or semi-absorbable hydrocolloids like potato starch. An increased amount of filler material will make the element stiffer while not compromising the softening of the contacting surface of the (cut) edge of the convex element and the resulting reduced friction according to the invention. Additionally or alternatively, the characteristics of the convex element may be further controlled by embossing or similarly treatment of the surface of at least the convex element. In this manner, the convex element may e.g. be reinforced to withstand higher pressure in the axial direction than in the radial direction while simultaneously providing improved comfort due to the softness of the material. The surface treatment of the convex element may, as an example, be applied by the convex shaped tool in a heat/vacuum moulding machine as described in any of the examples of positioning the convex element as described above.

In the context of this disclosure, the term "reacts to moisture" shall be understood as expressing that exposure to moisture or liquid water initiates a change at least in the physical characteristics of the material. Depending on the degree of moisture exposure and/or the dimensions of the convex element the described change can occur practically instantly and/or any time later. The change may occur wholly or partly in the material such as a softening of a part or a peripheral section of material. The "rate" of reaction to moisture of the material of the convex element according to the invention generally corresponds to an equivalent liner radial swelling of 0.5-3.0 mm of an element blank (provided with moisture-impenetratable material on its major surfaces) during an absorption time of 24 hours in a saline water solution.

In embodiments of the invention, the material reacting to moisture is a material that dissolves when exposed to moisture.

By this, a solid material comprised in the convex element becomes liquid or semi-liquid. In practice, only an innermost edge of the convex element abutting or being very close to the stoma's surface is affected, because it is only at that innermost edge that moisture can penetrate into the material of the convex element. This softens the convex element at the innermost edge and further has the effect that the liquid (or semi-liquid) material provides a lubricious interface with the stoma's surface, thereby reducing friction.

In embodiments, the material reacting to moisture is a material that swells when exposed to moisture.

By this, a swellable material in the form of a solid material comprised in the convex element expands or increases its size in one or more dimensions by the uptake of moisture, e.g. by absorption or adsorption. When the material expands, the material particles in the element tend to move or dislocate, if there is room for them to do so. As this in practice occurs primarily at the innermost edge of the convex element (where moisture uptake is), material particles typically expand radially inward towards the stoma and/or into contact with the stoma's surface. This means that an even closer fit to the stoma's surface or contour is achieved, which in turn increases security against leakage. In other words, the swellable material in the convex element has the ability to maintain the physical integrity of the convex element during moisture uptake contrary to a hydrocolloid-containing adhesive matrix normally disposed on the surface of a convex element which would relatively rapidly soften and/or even disintegrate.

In embodiments, the material reacting to moisture is a material that gels when exposed to moisture.

In these embodiments, the reaction to moisture is the occurrence of gelling. When a gelable material is exposed to moisture, the internal structure of the gelled material will have a weaker cohesion than any non-gelled part of the material. Thus, the physical characteristics of the material change as a reaction to such moisture exposure. One effect is that the material of the convex element in the gelled area, which area is at the innermost edge of the convex element, will be soft and have low friction. Another effect is that the gelled material creates a relatively closed layer (in the sense of being moisture-impermeable) on the peristomal skin surface between the innermost edge of the convex element and the stoma's surface or contour. Individually or in combination, these effects provide increased security against leakage.

In embodiments, the level of moisture absorption of the moisture reacting material of the convex element is equal to or less than the level of moisture absorption of the adhesive of the adhesive wafer.

Particularly suitable materials to achieve this effect include thermoplastic hydrocolloids. Thus, in embodiments the moisture reacting material is selected from the group of thermoplastic hydrocolloids. One example is Klucel® (hydroxypropylcellulose) from Ashland Company. As the level of moisture absorption of the moisture reacting material of the convex element may typically be lower than the moisture absorption level of the adhesive of the adhesive wafer, this means that the convex element has sufficient structural stiffness to maintain an adequate pressure on the peristomal skin surface during the normal weartime of the ostomy appliance. In other words, the adhesive of the adhesive wafer will be the limiting factor on the weartime.

In embodiments, the convex element comprises the same polymer material, or a polymer material with identical characteristics as the polymer material of the adhesive of the adhesive wafer.

It is noted that the elements described, in particular the convex element, are relatively easily cutable up to a thickness of generally 1.5 mm and further that any adaptive cutting is possible in both the convex element and the adhesive (and possibly further elements/layers) at the same time. This provides the user with an increased product flexibility since the stoma-receiving hole is adaptable even with a convex element included, contrary to known convex products wherein the stoma-receiving hole has to be pre-cut or custom-cut from the manufacturer. As described, this also allows the convex element to fully overlay the immediate peristomal skin area and letting the innermost edge of the element contact/abut, or almost contact the stoma's surface.

Described in an alternate wording, the invention relates to an ostomy appliance including a base plate, the base plate comprising a film and an adhesive disposed on a proximal surface of the film and adapted for attaching the base plate to skin of a user. A first hole is formed in the base plate and the appliance also includes a convex element attached to a distal surface of the film, a second hole formed in the convex element with the second hole having a diameter equal to a diameter of the first hole, and where the first and the second holes are co-axially aligned and the second hole formed in the convex element comprises a lubricating edge that changes from a solid state to a semi-liquid state when exposed to moisture.

In a second aspect, the invention relates to a base plate for an ostomy appliance, said base plate comprising an adhesive wafer comprising a top film and at least one skin-friendly adhesive on a proximal surface thereof for attaching the base plate to the skin of a user and having a first through-going hole, and a convex element being arranged distal to the user-interface of the adhesive wafer and having a second through-going hole of the same diameter as the first through-going hole and being co-axially arranged therewith, wherein the convex element comprises a material which reacts to moisture.

In embodiments, the convex element has a maintained convexity of at least 85% when exposed to a compression load corresponding to that required for pressing the convex element into a foam material such that the convex element is level with the foam surface. For further characteristics of such foam material, see the example part below. Particularly, the maintained convexity may be within 90-95%.

The materials, effects and embodiments described above in relation to the first aspect of the invention may be applied equally and/or similarly to, or in, the second aspect of the invention and vice versa.

In a third aspect, the invention relates to a convex element for use in a base plate for an ostomy appliance having a through-going hole being co-axially arranged with a stoma-receiving through-going hole in the base plate, wherein the convex element comprises a material which reacts to moisture.

The materials, effects and embodiments relating to the convex element and described above in relation to the first aspect of the invention may be applied equally and/or similarly to, or in, the third aspect of the invention and vice versa.

In a fourth aspect, the invention relates to the use of a material which reacts to moisture for forming a convex element for an ostomy appliance.

In embodiments, the material is made from a material composition blend.

The materials, effects and embodiments relating to the materials for such a convex element and described above in relation to the first aspect of the invention may be applied equally and/or similarly to, or in, the fourth aspect of the invention and vice versa.

DETAILED DESCRIPTION OF THE DRAWING

Initially, it shall be noted that the figures are schematic illustrations intended only to address the principles and functions of the base plate according to the invention and are not to be considered limiting to the scope of the attached claims. Furthermore, the figures and particularly the individually illustrated elements are not necessarily to scale, neither individually nor in relation to each other.

FIG. 1 illustrates an ostomy appliance 100 as known in the art with a standard "flat" base plate 101 and a collecting bag 102, the base plate typically comprising a top film carrying a skin-friendly adhesive on the proximal side facing the peristomal skin surface 103 surrounding a stoma 104. The base plate is shown in a situation just prior to a possible attachment to the skin of a user. The base plate also has a through-going stoma-receiving hole 105 allowing the stoma 104 to protrude into the bag 102 to deliver output from the stoma directly into the bag. Such a standard type "flat" base plate 101 is not well-suited for being placed around a stoma 104 situated in a skin surface recess 107. This is at least partly because the skin surface in such a recess is often moved, bent, stretched, folded or otherwise subject to change in its topography which is due to the user's body movements and also to peristaltic movements of the intestines. Furthermore, the peristomal skin surface may often also be scarred or bruised from one or more surgeries. Since the standard "flat" base plate 101 does not have dedicated means for providing a pressure to the peristomal skin surface it cannot adequately maintain the base plate in place on the skin surface, whereby the risk of stomal output ending up underneath the adhesive surface is increased and leakage problems are often the consequence.

Figure 2:
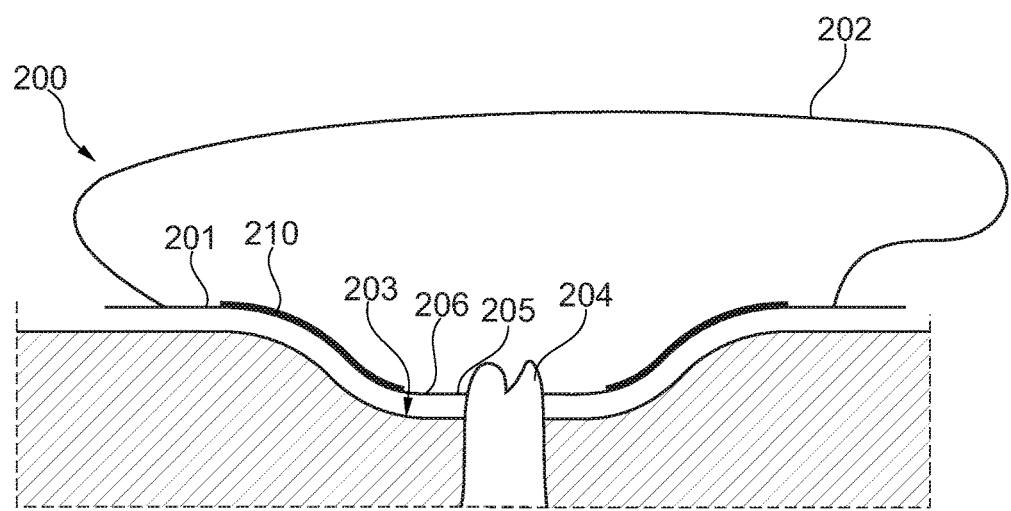
FIG. 2 is a schematic cross-sectional view of an ostomy appliance having a traditional rigid or stiff convex element to address the challenges of a stoma in a recess.

FIG. 2 shows an ostomy appliance 200 with a collecting bag 202 and a base plate 201 similar to the base plate 101 of FIG. 1 except that it further comprises a convex element 210 on the distal side of the base plate 201. The convex element 210 is stiff or rigid and may e.g. be cast in a mould to obtain the specific convex shape before being attached to the base plate 201 e.g. by gluing or welding. The appliance is shown in a situation just prior to attachment to a peristomal skin surface 203. As it can be understood from the cross-sectional illustration, the convex element 210 does not cover or overlay the innermost part 206 of the base plate 201 immediately surrounding the stoma 204. If this was the case, then it would not be possible for the user to customize the stoma-receiving hole 205 in the base plate 201, because it is not possible to cut the stiff or rigid convex element 210. Leaving this innermost part 206 of the base plate 201 free from contact with, or influence by, the pressure inducing convex element 210, has the consequence that the base plate 201 may not be held adequately in contact with the peristomal skin surface, whereby similar risks of leakages as described above are encountered.

Figure 3:
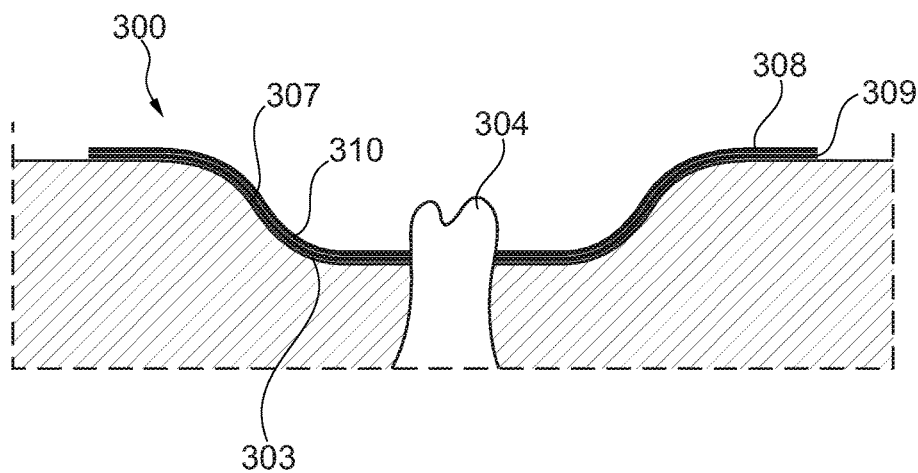
FIG. 3 is a schematic cross-sectional view of a base plate for an ostomy appliance of the soft convex-type in an idealistic situation immediately after attachment to the peristomal skin surface.

FIG. 3 shows a base plate 300 for an ostomy appliance of a soft convex-type attached to a peristomal skin surface 303 around a stoma 304 situated in a recess 307 of the skin surface. The base plate 300 comprises a thermoplastic top film 308 and an adhesive 309 facing the skin surface. The thermoplastic top film is thermoformed in production to obtain the convex shape and thus for this kind of appliance, the convex thermoformed top film is forming, or can be said to form, the convex element 310 of the appliance. FIG. 3 may be seen as illustrating a situation immediately after attachment of the base plate to the peristomal skin surface 303 wherein the stoma 304 protrudes axially and distally away from the user-interface of the adhesive wafer and is able to deliver stomal output directly into a collecting bag (not shown).

Figure 4:
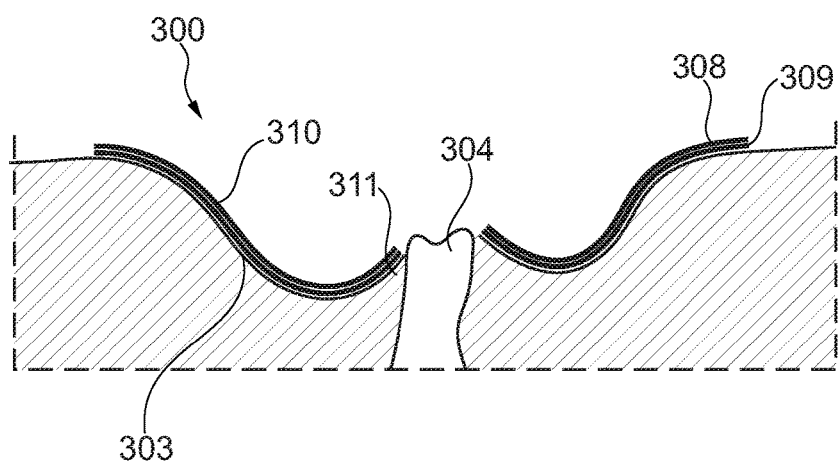
FIG. 4 is a schematic cross-sectional view of the soft convex base plate of FIG. 3 intended to illustrate the limitations of such a product type.

FIG. 4 also shows the soft convex base plate 300 of FIG. 3 and further illustrates one limitation of this kind of base plate. The convex element 310 provided by the thermoformed top film 308 is unable to maintain an adequate pressure on the peristomal skin surface 303. Because of the user's normal body movements, also causing changes in the topography of the user's skin, e.g. bulges, the base plate 300 may be axially and distally dislocated from the original level, typically in a skin area 311 immediately around the stoma 304. Furthermore, due to the peristaltic movements of the intestines and thereby the stoma 304, and also because of the body movements mentioned, the stoma 304 may retract in a proximal direction thereby coming into level with, or even below, the surrounding skin area 311. Since there is a lack of adequate pressure on the peristomal skin due to the limitations of the soft convex base plate, there is nothing to prevent the stoma 304 from retracting in such a manner. When the stoma 304 is in this way retracted, stomal output may easily flow underneath the top film 308 and attack and/or disintegrate the adhesive 309 leading to leakage problems as already described.

Figure 5:
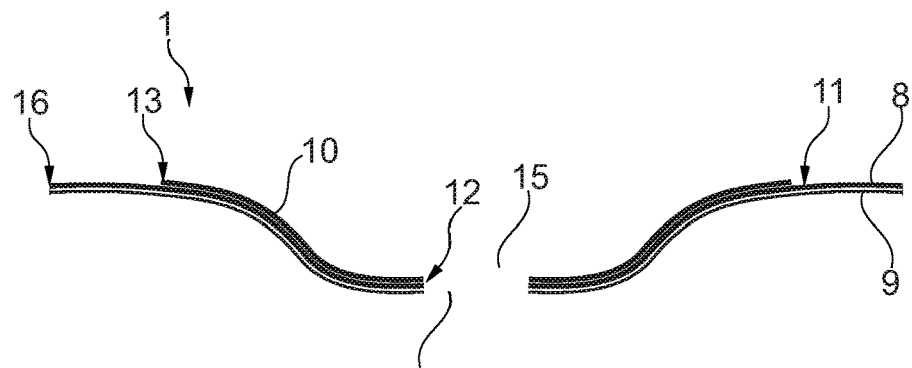
FIG. 5 is a slightly exploded schematic cross-sectional view of a base plate for an ostomy appliance comprising a convex element according to the invention.

FIG. 5 shows a base plate 1 of a one-piece or two-piece ostomy appliance (collecting bag not shown) according to the invention. The base plate 1 has a convex element 10 attached to a distal surface of an adhesive wafer 11, i.e. the convex element 10 is arranged distally to the user-interface of the adhesive wafer 11. The adhesive wafer 11 comprises a top film 8 having at least a first skin-friendly adhesive 9 disposed on the proximal surface thereof. As it can be seen, the convex element 10 covers or overlays the wafer 11 from an inner periphery 12 of the wafer 11, corresponding to a first through-going hole 5 in the wafer 11 and building a stoma-receiving opening, to an outer periphery 13 of the convex element 10. The proximal surface of the convex element 10 is attached to the distal surface of the top film 8 at least at, or close to, the inner and outer peripheries of the convex element 11 and may be attached further also between these peripheries. The outer periphery 13 of the convex element 10 is shown in a position radially inwardly of an outer boundary 16 of the wafer 11, but may alternatively coincide therewith. The inner periphery of the convex element 10 defines a second through-going hole 15.

Figure 6:
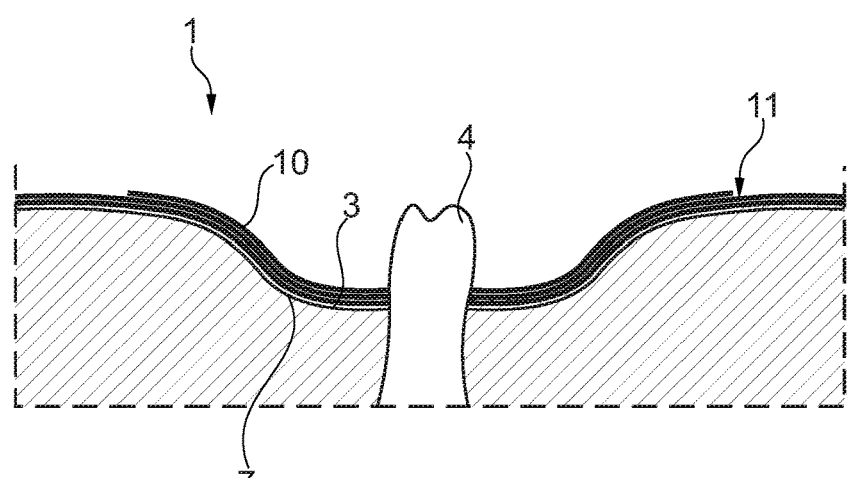
FIG. 6 is a schematic cross-sectional view illustrating the base plate of FIG. 5 attached to the peristomal skin surface around a stoma in a recess.

FIG. 6 shows the base plate 1 of FIG. 5 according to the invention positioned in place in a use situation in a skin recess 7 surrounding a stoma 4 on the skin surface of a user.

The base plate 1, including the wafer 11 and the convex element 10, surrounds the stoma 4 and covers, or nearly covers, the immediate peristomal skin surface 3. The first stoma-receiving hole 5 in the wafer 11 is arranged co-axially with the second through-going hole 15 in the convex element 10 making up a stoma-receiving opening, which opening may be optimally size-customized by a user (before attachment to the skin), since the characteristics of the convex element 10 (and the wafer 11) allows cutting e.g. by means of scissors. Thereby, the base plate 1 may fit optimally in the recess 7 around the stoma 4 and even abut, or contact, the stoma's surface without damaging or irritating the stoma 4.

Simultaneously, the convex element 10 provides an adequate and necessary pressure on the skin over the whole area of the immediate peristomal skin surface 3 (i.e. completely to abut or contact the stoma 4) to keep the adhesive 9 in contact with the peristomal skin surface 3 and to make the stoma 4 protrude sufficiently past the user-interface of the wafer 11 at all times. Providing pressure so close to the stoma 4 is not possible with the convex ostomy appliances on the market today, and the invention thus provides an improved safety against stomal output emerging from the opening in the stoma 4 ending up underneath the wafer 11, where the aggressive output may otherwise easily break or disintegrate the adhesive 9 leading to complete failure of the product (e.g. disconnection from the skin).

Figure 7:
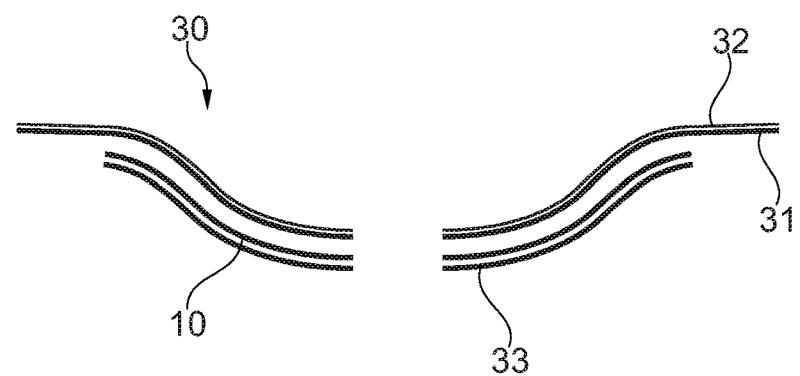
FIG. 7 is a slightly exploded schematic cross-sectional view of an alternative embodiment of a base plate comprising a convex element according to the invention.

FIG. 7 schematically shows another example of a base plate 30 according to the invention. In this example, the distal surface of the convex element 10 is attached to a first skin friendly adhesive 31 provided on the proximal surface of a top film 32 while a second skin-friendly adhesive 33 is provided at least on the proximal surface of the convex element 10. Thereby, the convex element 10 is arranged distally to the user-interface of the adhesive wafer. The example of FIG. 7 otherwise works in the same manner and has the same effects and benefits according to the invention as described for the example of FIG. 6.

Example

In order to effectively illustrate the basic principle of the present invention, i.e. to provide a convex ostomy product that is able to maintain adequate pressure on the peristomal skin while being hole-size customizable, a test series has been carried out. The test results basically show the difference in depth of the convexity of a test specimen i) before being exposed to any load and ii) in a simulated use situation.

Test Specimens

Coloplast SenSura Convex Light was used in the test as a reference product and is a commercially available convex ostomy appliance, e.g. for relatively shallow peristomal skin surfaces, and normally recognised as a convex product solution having a flexibility ranging between the appliances having a pre-cast or moulded convex element and the soft convex appliances as described in the background section. Further information on the material for the convex element of Coloplast SenSura Convex Light can be found in applicant's published application WO 2002/094333.

Convatec Mouldable Convex is another commercially available ostomy appliance which was also used in the test as a reference product. The product includes the Convatec Mouldable Technology™ skin barrier which enables the barrier material to be fitted close both to the stoma's surface and to the peristomal skin surface.

Sample 1 "Soft" and sample 2 "Hard" are sample base plates for an ostomy appliance comprising a convex element according to the invention with material compositions as listed in table 1 below:

TABLE 1

| Raw material | Function | Sample 1 "Soft" [%] | Sample 2 "Hard" [%] |
|---|---|---|---|
| LLDPE | Stiffness | 30 | 40 |
| EVA-Levamelt 700 | Soft | 20 | 10 |
| CMC | Absorption | 10 | 10 |
| Potato starch | Filler | 40 | 40 |
| Total | | 100 | 100 |

The LLDPE (linear low-density polyethylene) material used was a product no. FA6224 from *Borealis* AG, Austria. The EVA material used was a Levamelt 700 from Lanxess, Germany. CMC is carboxymethyl cellulose.

Preparations

Test samples 1 and 2 were prepared in the following way: first the materials were mixed, then heat pressed and then cut out to an element blank. Then the element blank was combined with the other parts of the base plate and subsequently provided with its convexity as further described in the examples above.

For the mixing procedure, 200 g of the desired recipe is mixed in a Z-blade mixer at 140° C. for 30 min at a speed of 25 rpm under vacuum. Initially, the EVA is melted for 2 min in the mixer—then the LLDPE is added and mixed with the EVA for 10 min. Then, CMC and potato starch is added and mixed with the EVA/LLDPE for an additional 12 min.

The mixture from the mixing explained above is heat pressed at 120° C. to a thickness of 2 mm and then cut to an oval element blank of 80×70 mm.

The adhesive wafer is constructed using a top film of polyurethane film of 40µ thickness (e.g. Bioflex from Scapa medical) having disposed on one side thereof a layer of the second skin-friendly adhesive type as described above covering a minimum surface area of 130×110 mm. Then the heat pressed element blank of 80×70×2 mm for the convex element material according to the invention is centered on the oval adhesive. Then a layer (approximately 1000µ thickness) of the first skin-friendly adhesive type as described above is placed on the element blank. As the last item, a peelable APET release liner of 150µ thickness from Huhtamaki is placed on the adhesive surface.

This combined construction is moulded by means of heat (140° C. for 30 seconds) by use of a vacuum mould in order to achieve the convex shape. A base plate for an ostomy appliance comprising the convex element according to the invention is then punched out to the desired size (such as 120×100 mm) and finally a through-going pre-cut center hole is punched or cut in the base plate.

Test Procedure and Conditions

The test was performed at a temperature of 23° C. and at approx. 50% RH. The depth of the initial convexity was measured by applying the distal surface of the base plate to a hard substrate and placing a metal plate on "top" of the convex portion, i.e. so as to contact at least on a portion of the proximal surface of the base plate surrounding the stoma-receiving through-going hole. A caliper was then used for measuring the distance between the substrate and the downward facing surface of the metal plate through the stoma-receiving through-going hole(s) and this value constitutes the initial convexity depth.

The depth of the convexity under load was measured by placing the proximal surface of the base plate on a foam material substrate to simulate conditions on the skin surface (abdomen) of a user and provide a compression load on at least a portion of the distal surface of the base plate (the portion corresponding to at least a part of the distal surface not being convex). The compression load is increased until a proximal surface of the non-convex part of the base plate is level with the surface of the foam material. Then, the loaded convexity depth is measured as the resulting distance between the surface level of the foam and the distal surface of the base plate at the innermost edge surrounding the through-going hole (measured along the axis of the through-going hole) when the base plate is pressed into the foam. As above, this is measured by means of a caliper. The ratio of the loaded convexity depth to the initial convexity depth defines a measure for the maintained convexity of the convex element when exposed to load.

It can be shown that the depths measured on a foam material correspond closely to those obtainable by placing the test specimens on an abdomen of a real user. However, for the sake of reproducibility at least, the foam material was chosen as the basis for comparison. The foam material used in the test was a polyether material with thickness of 40 mm. To further characterise the foam material, the following is noted: an average load of 2.6N was obtained by submitting the foam material to 10 mm compression by means of an Ø20 mm probe when placed on a hard substrate.

Test Results

TABLE 2

| Specimen | Diameter of pre-cut hole [mm] | Depth of initial convexity [mm] | Depth of loaded convexity [mm] | Maintained convexity [%] after load |
|---|---|---|---|---|
| Coloplast SenSura Convex Light | 22 | 5.7 | 3.5 | 61.4 |
| Convatec Mouldable | 20 | 7.0 | 3.2 | 45.7 |
| Sample 1 "Soft" | 20 | 8.5 | 7.8 | 91.8 |
| Sample 2 "Hard" | 20 | 8.5 | 8.0 | 94.1 |

As it may be understood from the test results presented in the table above, the base plate comprising the convex element according to the invention maintains a significantly higher degree of its initial convexity after being submitted to load than the reference products, while still being customizable to closely fit to the stoma's surface at very little or no risk of the innermost edge of the convex element cutting or otherwise harming the stoma. Thereby, it is understood that a base plate comprising a convex element according to the invention is able to incur a higher reactive force to the peristomal skin of a user than the reference products. This means that the ability to keep the stoma adequately protruding above the surrounding skin level is increased and the risk of stomal output ending up underneath the adhesive in the immediate peristomal area is therefore significantly reduced or eliminated.

The invention claimed is:

1. An ostomy appliance comprising a base plate, the base plate comprising:
   an adhesive wafer having a first adhesive on a proximal surface of a backing layer, where a proximal surface of the first adhesive forms a user-interface adapted for attachment of the base plate to skin around a stoma of a user, the adhesive wafer having a first through-going hole with a first diameter; and
   a convex element connected to the adhesive wafer, the convex element located distal to the user-interface of the adhesive wafer, the convex element having a second through-going hole that forms an innermost edge of the convex element, with the first through-going hole and the second through-going hole adaptable to be sized to fit around a stoma of the user and the second through-going hole is co-axial with the first through-going;

wherein the convex element has a thickness measured between a proximal side and a distal side of the convex element, and the thickness of the convex element measured from the innermost edge of the convex element to an outermost perimeter of the convex element is substantially uniform;

wherein the convex element comprises a second adhesive provided at least at the innermost edge that reacts to moisture by one of dissolving when exposed to moisture, swelling when exposed to moisture, and forming a gel when exposed to moisture such that the innermost edge of the second through-going hole provides a lubricating surface when exposed to moisture from the stoma;

wherein the convex element has a depth of convexity that is greater than the thickness of the convex element.

2. The ostomy appliance according to claim 1, wherein the convex element is attached to the backing layer.

3. The ostomy appliance according to claim 1, wherein the convex element is embedded between the first adhesive layer connected to the backing layer and a third adhesive layer located on a side opposite from the first adhesive layer.

4. The ostomy appliance according to claim 1, wherein a level of moisture absorption of the convex element is equal to or less than a level of moisture absorption of the first adhesive.

5. The ostomy appliance according to claim 1, wherein the second adhesive is a thermoplastic hydrocolloid.

6. The ostomy appliance according to claim 1, wherein the second adhesive of the convex element and the first adhesive are formed from identical polymer materials.

7. The ostomy appliance according to claim 1, wherein the convex element comprises one or more polyethylene based polymers; one or more ethylene vinyl A acetate-based polymers; one or more hydrocolloid powders; one or more hydrophilic polyurethane-based polymers; one or more filler materials and one or more water swellable/soluble polymers.

8. The ostomy appliance according to claim 1, wherein a portion of the proximal side of the convex element is formed to be convex and a portion of the distal side of the convex element is formed to be concave.

9. The ostomy appliance according to claim 1, wherein the convex element is connected to the backing layer, and the convex element is concave on a side of the convex element that is farthest way from the backing layer.

10. The ostomy appliance according to claim 1, wherein the innermost edge of the second through-going hole of the convex element is adapted to change from a solid state to a semi-liquid state when exposed to the moisture of the stoma.

11. The ostomy appliance according to claim 1, wherein the second through-going hole is co-axial with the first through-going hole such that, when the base plate is applied to the skin of the user, the convex element is configured to overlay a peristomal skin area around the stoma.

12. The ostomy appliance according to claim 1, wherein the ostomy appliance is a one-piece appliance with an ostomy bag connected to the base plate.

13. The ostomy appliance according to claim 1, wherein the convex element provides a convexity to the adhesive wafer and to the base plate, and the convex element is adapted to maintain more than 75% of the convexity of the base plate when the base plate is exposed to an axial load of 2.6 Newtons.

14. The ostomy appliance according to claim 1, wherein a first portion of the proximal side of the convex element adjacent to the innermost edge of the second through-going hole is formed to be convex and a second portion of the proximal side of the convex element adjacent to the outermost perimeter of the convex element is formed to be concave.

15. An ostomy appliance base plate comprising:
a backing film;
a first adhesive coupled to a proximal side the backing film with the first adhesive configured to secure the ostomy appliance around a stoma of a user;
a convex element connected directly to one of the backing film and the first adhesive; and
a through-going hole formed through the backing film, the first adhesive, and the convex element;
wherein a thickness measured between a proximal side and a distal side of the convex element is approximately uniform, and the convex element is formed to have a depth of convexity that is greater than the thickness of the convex element;
wherein the convex element is moisture reactive such that an innermost edge of the through-going hole of the convex element provides a lubricating surface when exposed to moisture of the stoma.

16. The ostomy appliance base plate of claim 15, wherein the first adhesive contacts a proximal side of the backing film and the convex element contacts a distal side of the backing film.

17. The ostomy appliance base plate of claim 15, wherein the convex element is located between the first adhesive and the backing film.

18. The ostomy appliance base plate of claim 15, wherein the convex element is formed from a second adhesive, and the second adhesive is identical to the first adhesive coupled to the backing film.

19. The ostomy appliance base plate of claim 15, further comprising an ostomy bag connected to a distal side of the backing film.

20. The ostomy appliance according to claim 15, wherein a first portion of the proximal side of the convex element adjacent to the through-going hole is formed to be convex and a second portion of the proximal side of the convex element adjacent to an outermost perimeter of the convex element is formed to be concave.

* * * * *